United States Patent
Buitink et al.

(10) Patent No.: US 9,914,107 B2
(45) Date of Patent: *Mar. 13, 2018

(54) UREA PLANT REVAMPING METHOD

(71) Applicant: Stamicarbon B.V., Sittard (NL)

(72) Inventors: Fredericus Henricus Maria Buitink, Sittard (NL); Luc Louis Maria Dieltjens, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,680

(22) PCT Filed: Dec. 27, 2013

(86) PCT No.: PCT/NL2013/050960
§ 371 (c)(1),
(2) Date: Jun. 25, 2015

(87) PCT Pub. No.: WO2014/104893
PCT Pub. Date: Jul. 3, 2014

(65) Prior Publication Data
US 2015/0343409 A1     Dec. 3, 2015

(30) Foreign Application Priority Data
Dec. 28, 2012  (EP) .................................. 12199620

(51) Int. Cl.
*B01J 19/00*   (2006.01)
*B01D 3/00*    (2006.01)
*C07C 273/04*  (2006.01)

(52) U.S. Cl.
CPC .............. *B01J 19/00* (2013.01); *B01D 3/009* (2013.01); *C07C 273/04* (2013.01); *B01J 2219/0004* (2013.01); *B01J 2219/00024* (2013.01); *B01J 2219/00027* (2013.01); *B01J 2219/185* (2013.01); *Y10T 29/49718* (2015.01)

(58) Field of Classification Search
CPC ..................... C07C 273/04; B01J 19/00; B01J 2219/00027; B01J 2219/00024; B01J 2219/0004; B01J 2219/185; B01D 3/009; Y10T 29/49718
See application file for complete search history.

(56) References Cited

U.S. PATENT DOCUMENTS
7,347,903 B2    3/2008  Yamadera et al.

FOREIGN PATENT DOCUMENTS
WO    WO-95/00674    1/1995
WO    WO-96/20170    7/1996

OTHER PUBLICATIONS
International Search Report for PCT/NL2013/050960, dated Feb. 10, 2014, 3 pages.

*Primary Examiner* — Daniel C McCracken
(74) *Attorney, Agent, or Firm* — Morrison & Foerster LLP

(57) ABSTRACT

Disclosed is a method of increasing the capacity of an existing urea plant. With reference to the regular components of a urea plant, including a synthesis section comprising a high pressure carbamate condenser and a reactor, and a recovery section, the method comprises installing an additional reactor between the recovery section and the high pressure carbamate condenser. The additional reactor is preferably installed in connection with an ejector, so as to allow ground placement of the additional reactor.

7 Claims, 4 Drawing Sheets

UREA PLANT REVAMPING METHOD

CROSS-REFERENCE TO RELATED APPLICATIONS

This application is the national phase of PCT application PCT/NL2013/050960 having an international filing date of 27 Dec. 2013, which claims benefit of European patent application No. 12199620.1 filed 28 Dec. 2012. The contents of the above patent applications are incorporated by reference herein in their entirety.

FIELD OF THE INVENTION

The invention is in the field of urea production, and particularly pertains to a process of increasing the production capacity of an existing urea plant.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

$$2NH_3 + CO_2 \rightarrow H_2N\text{—}CO\text{—}ONH_4$$

after which the ammonium carbamate formed is dehydrated in the second step to give urea according to the endothermic equilibrium reaction:

$$H_2N\text{—}CO\text{—}ONH_4 \leftrightarrow H_2N\text{—}CO\text{—}NH_2 + H_2O$$

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone. In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa. In the art, these ranges are generally considered to represent "high pressure" (as also used in connection with a conventional "High Pressure Carbamate Condenser"). The ammonia to carbon dioxide molar ratio (N/C ratio) in the urea synthesis zone of a stripping plant lies usually in between 2.2 and 5 and preferably between 2.5 and 4.5 mol/mol. The synthesis zone can be carried out in a single reactor or in a plurality of reactors arranged in parallel or series.

After the stripping treatment, the pressure of the stripped urea solution is reduced in a urea recovery section. In a recovery section the non-converted ammonia and carbon dioxide in the urea solution is separated from the urea and water solution. A recovery section comprises usually a heater, a liquid/gas separation section and a condenser. The urea solution entering a recovery section is heated to vaporize the volatile components ammonia and carbon dioxide from that solution. The heating agent used in the heater is usually steam. The formed vapor in said heater is separated from the aqueous urea solution in the liquid/gas whereafter said vapor is condensed in the condenser to form a carbamate solution. The released condensation heat is usually dissipated in cooling water. The formed carbamate solution in that recovery section operated at a lower pressure than the pressure in the synthesis section is preferably returned to the urea synthesis section operating at synthesis pressure. The recovery section is generally a single section or can be a plurality of recovery sections arranged in series.

Many urea production facilities exist. When increasing demands of urea production are to be met, methods are sought to increase the capacity of existing plants, rather than building new ones. The same holds for the continuous desire to have urea plants operate in more energy-efficient ways. Increasing the capacity of a plant is sometimes also referred to as "de-bottlenecking". For, one will frequently increase the capacity of one part of the plant (e.g. the reactor), to then find that the resulting increased capacity cannot be accommodated by one or more other sections of the plant (e.g. the carbamate condenser). Various solutions have been proposed in the art to satisfy one or more of the foregoing desires.

Conventional ways of increasing the reactor volume are known in the art. For example it is possible to increase the reactor volume of an existing reactor by extending the reactor itself. This can be done by cutting the upper hemi-head of the reactor and placing a cylindrical part between the existing hemi-head and the bottom part of the reactor. Subsequently the pieces can be welded in place. A disadvantage of this method is that the expansion possibility is limited due to the significant addition of height which is typically limited by regulations and also the additional requirement of reinforcing the structure which supports the reactor. Another known method to add an additional reactor in series, but this has similar disadvantages. A third method for increasing the capacity is by replacing the HPCC with a pool condenser, but this requires a complicated equipment design.

As further background art, reference is made to WO 96/20170. Herein, in a process for urea production, a urea reaction mixture is obtained in a main reaction space. The reaction mixture is subjected to stripping and then sent to a recovery section. A carbamate stream from the recovery section is recycled to an auxiliary reaction space. Therein carbamate is converted to urea. The urea liquid stream from the auxiliary reaction space is sent to the stripper. The entire gas stream from the stripper is sent to the condenser.

SUMMARY OF THE INVENTION

In order to better address one or more of the foregoing desires, the invention provides a method of increasing the production capacity of an existing urea plant, the existing plant comprising a high pressure carbamate condenser, a reactor, a stripper, and a recovery section, wherein:
the condenser comprises a liquid outlet in fluid communication with a liquid inlet of the reactor;
the reactor comprises a liquid outlet in fluid communication with the stripper;
the stripper comprises a gas outlet in fluid communication with a gas inlet of the condenser and a liquid outlet in fluid communication with the recovery section;
the recovery section comprises a liquid outlet in fluid communication with a liquid inlet of the condenser;
the method comprising installing an additional reactor and flow lines, such that the additional reactor has a liquid inlet that is in fluid communication with the liquid outlet of the recovery section; said additional reactor comprising a liquid outlet in fluid communication with an inlet to a condensation chamber of the condenser.

DETAILED DESCRIPTION OF THE INVENTION

Figure 1:
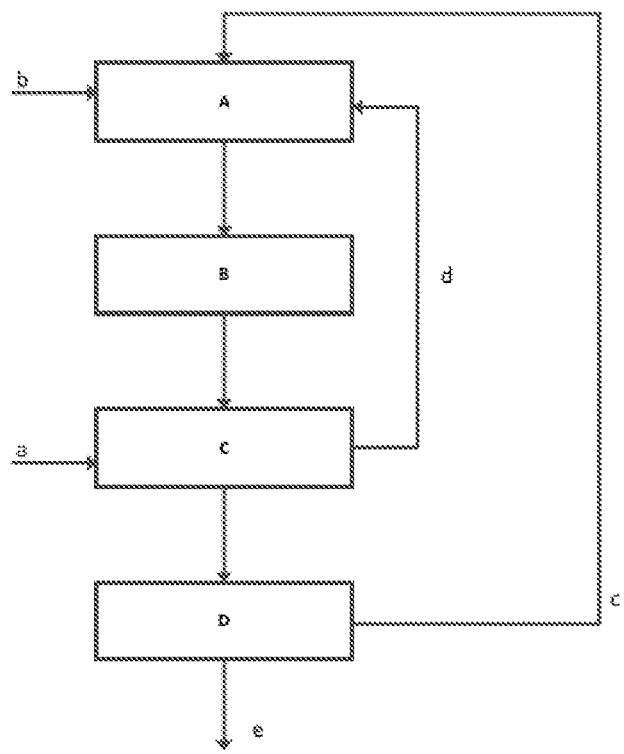
FIG. 1 and FIG. 2 are block diagrams representing in FIG. 1 a conventional plant and in FIG. 2 a corresponding plant resulting from the revamping method of the invention.

In a broad sense, the invention is based on the judicious insight that the production capacity of an existing urea plant can be increased in an entirely different way than by enlarging the synthesis section. The latter refers to the classical ways of dealing with an increase in production capacity. One is installing an additional reactor downstream of the already present reactor in a urea plant. This amounts to enlarging the production capacity of the urea synthesis section. Such an additional reactor forms the revamp alternative to just building a new plant having a larger reactor. Another such revamp alternative to just building a new reactor, is proving an extension to the existing reactor (thus, in fact, enlarging it). The present invention adds a reactor in a totally different section of the urea plant, viz. directly after the recovery section. Moreover, the present invention does not merely add a urea reactor, which operates on the basis of the classical feed streams in a urea plant, but a reactor that is specifically to be fed with carbamate solution (i.e. operating so as to conduct only the second stage of urea synthesis, as outlined above).

The invention not only provides benefits in the sense of increasing the urea production capacity. It has surprisingly been found that the installation of an additional urea reactor in accordance with the invention increases the steam pressure in the high pressure carbamate condenser (HPCC). Without wishing to be bound by theory, the inventors believe that this is caused by the presence of significant amounts of urea in the HPCC, thereby increasing the operating temperature of the HPCC. As a result the pressure in the HPCC will be higher. The higher pressure steam may be exchanged for increasing capacity or used to save energy. Also a higher conversion into urea is seen.

The foregoing is reflected in the requirement that the additional reactor comprises a liquid outlet in fluid communication with an inlet to a condensation chamber of the condenser.

It will be understood that a condensation chamber is the space of a condenser wherein normally gas enters, and is then condensed to liquid, in said condensation chamber. The liquid outlet of the additional reactor is thus in fluid communication with an inlet to the condenser that, normally, would be a gas inlet. E.g., in the event of a shell and tube condenser, the condensation chamber typically is the shell-side thereof. One would normally recognize that liquid (viz. cooling liquid) is sent to the tube-side of the condenser, and gas (to be condensed) is sent to the shell-side. In the present invention, the specific liquid identified, viz. the urea solution produced in the additional reactor, is sent to the condensation chamber, such as the shell-side of a shell-and-tube condenser.

Further, in the process of the invention preferably only a part of the stripper gas is sent to the condenser, the remainder is sent to the additional reactor. This serves to provide heat to the additional reactor and increase the urea conversion.

The specific steam consumption of the urea process of the invention will be lower. A particular advantage of the invention is that the additional reactor may be positioned on the ground floor. This reduces the need for significant structural support. A further advantage is that the additional reactor may be of a simple design, for example a vertical tower with trays.

The additional reactor is sometimes also described as a "pre-reactor" or a "Urea Pre-Reactor" (UPR).

In a preferred embodiment of the invention, the additional reactor is operated in countercurrent mode; that is, the liquid is entered at the top and flows down, whereas the gas-feed is entered into the bottom and rises up in countercurrent to the descending liquid. It has surprisingly been found that this mode of operation allows for a higher degree of conversion in the additional reactor as compared to the more usual co-current mode of operation for vertical urea reactors. It is believed that the main reason for this higher conversion is given in the fact that in counter-current mode of operation the liquid is withdrawn from the bottom of the reactor, whereas in the bottom the gas phase contains the lowest amount of non-condensables and the lowest content of light components in the gas-phase is observed.

In the revamped plant of the invention, the recovered carbamate solution is subjected to urea forming conditions. These conditions generally entail an operating pressure between 12 and 18 MPa, and a temperature of from 160° C. to 210° C., preferably of from 175° C. to 190° C. The pressure preferably is between 13 and 16 MPa.

It is conceivable to build a new plant (sometimes referred to as "grassroots" plant) based on the design of the present invention. This would provide the aforementioned advantages in terms of steam efficiency and urea conversion. However, it will be understood that the advantage of increasing of the urea production capacity, does not play a role in the case of grassroots plants. This typically plays a role in revamping existing plants.

The revamp method of the invention particularly serves to increase the production capacity of the urea plant, after the revamp, as compared to the production capacity of the same plant, before the revamp. The key to this, according to the invention, is installing the additional reactor as outlined above. I.e., an additional reactor positioned between the recovery section and the high pressure carbamate condenser present in the existing plant.

In this description reference is made to the production capacity of a urea plant. This refers to the volume of urea that can be produced in a given time period. More specifically, the invention pertains to increasing the production capacity of a urea plant by increasing the available reactor volume for urea synthesis.

In the definition of a plant, reference is sometimes made to the terms "liquid outlet," gas outlet" and the corresponding inlets. It will be understood that a "liquid outlet" is an outlet through which liquid can flow, and a "gas outlet" is an outlet through which gas can flow. The same holds for the respective inlets. The types of outlets and inlets available for either or both of these purposes are fully familiar to the skilled person.

Flow lines, for gas and/or liquid, are generally provided in the form of suitable piping.

Fluid communication refers to an arrangement connecting two parts of a plant via a gas or liquid flow line, in a such a way that a fluid (being a gas, a liquid, or a supercritical liquid) can be transported from one to the other.

A particular advantage of the invention is that the additional reactor may be positioned on the ground floor. This reduces the need for significant structural support. To this end, an ejector is placed downstream of the additional reactor. The ejector (which, as known to the skilled person, serves to provide a pumping function without mechanical means) is placed downstream of the additional reactor. I.e. particularly between the additional reactor and the high pressure carbamate condenser.

In another preferred embodiment of the plant resulting from the invention, a high pressure scrubber is positioned between the urea recovery section and the additional reactor. In this embodiment, the invention advantageously combines the use of the carbamate recycle stream as a scrubbing liquid, with the production of urea in the additional reactor. The carbamate recycle stream, upon acting as a scrubbing liquid will become enriched in carbon dioxide and ammonia by absorbing this from the reactor overhead gas stream. The carbamate recycle stream thereby effectively becomes more concentrated. As a result, said stream will in turn produce more urea in the additional reactor.

The additional reactor—similarly to the conventional reactor—preferably is a vertical reactor. This provides a space advantage, as such a reactor provides the smallest thinkable footprint. The additional urea reactor may be of a simple design, for example a vertical tower with trays.

In a preferred embodiment of the invention, the additional reactor is operated in countercurrent mode; that is, the liquid is entered at the top and flows down, whereas the gas-feed is entered into the bottom and rises up countercurrent to the descending liquid. It has surprisingly been found that this mode of operation allows for a higher degree of conversion in the additional reactor as compared to the more usual co-current mode of operation for vertical urea reactors. It is believed that the main reason for this higher conversion is given in the fact that in counter-current mode of operation the liquid is withdrawn from the bottom of the reactor, whereas in the bottom the gas phase contains the lowest amount of non-condensables and the lowest content of light components in the gas-phase is observed.

The urea plant of the invention, apart from the additional reactor, can be just any urea plant based on stripping with either ammonia or carbon dioxide. Also a thermal stripping plant may be used as a starting plant. An overview of commercial processes for producing urea is given, e.g., in Ullmann Encyclopedia, 2005 Wiley-VCH Verlag, Weinheim, Germany, chapter "Urea."

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution.

Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

The invention is not limited to any particular urea production process. Other processes and plants include those that are based on technology such as the HEC process developed by Urea Casale, the ACES process developed by Toyo Engineering Corporation and the process developed by Saipem (formerly Snamprogetti).

The additional reactor placed in accordance with the invention can be of a standard type. A reactor generally is a vessel provided with the appropriate inlets and outlets, and provisions for controlling temperature an pressure. Particularly, the additional reactor of the present invention is made so as to be operated under the aforementioned high pressure urea synthesis conditions. In view of the generally corrosive environment, the additional reactor is preferably made of a highly corrosion-resistant type of steel. The latter particularly refers to duplex steels, and more particularly to duplex ferritic-austenitic stainless steel having a high content of Cr and N, and a low content of Ni. A reference in this respect is WO 95/00674. In another preferred embodiment, the additional reactor (and particularly the inner parts thereof) is made of a duplex stainless steel consisting of, in percent by weight, C: 0.03% or less, Si: 0.5% or less, Mn: 2% or less, P: 0.04% or less, S: 0.003% or less, Cr: 26% or more, but less than 28%, Ni: 7.3-10%, Mo: 0.2-1.7%, W: more than 2%, but no more than 3%, N: more than 0.3%, but no more than 0.4%, with the balance being Fe and impurities, in which the content of Cu as an impurity is not more than 0.1%. This steel is described in U.S. Pat. No. 7,347,903.

The preferred additional reactor is made from a duplex, stainless steel alloy, containing, in percent by weight:
C: maximally 0.05%, preferably maximally 0.03%;
Si maximally 0.8%, preferably maximally 0.5;
Mn 0.3-4%, preferably 0.3-1%;
Cr 28-35%, preferably 29-33%;
Ni 3-10%;
Mo 1.0-4.0%, preferably 1.0-1.3%;
N 0.2-0.6%, preferably 0.36-0.55%;
Cu maximally 1.0%;
W maximally 2.0%;
S maximally 0.01%;
Ce 0-0.2%;
the remainder being Fe and normally occurring impurities and additives, the ferrite content being 30-70% by volume, preferably 33-35% by volume.

The invention is hereinafter illustrated with reference to the drawings. The drawings are for illustration purposes, and are not intended to be limiting to the invention.

Legend

Figure 2:
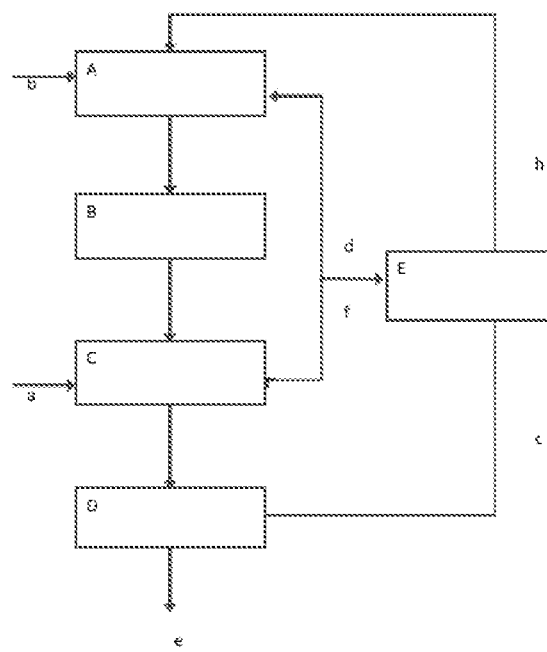

In the drawings, the capital letters (A-E) indicate components of a urea plant. The small letters (a-f) indicate streams. The legend is as follows:
A=High pressure carbamate condenser
B=High pressure reactor
C=High pressure stripper
D=Urea recovery section
E=Urea pre-reactor (UPR)
F=High pressure Scrubber
a=Ammonia
b=Carbon Dioxide
c=Carbamate recycle
d=Strip gas
e=Urea
f=Stripgas to UPR
g=Concentrated carbamate recycle
h=Urea stream from UPR FIG. 1 and FIG. 2 are block diagrams representing in FIG. 1 a conventional plant and in FIG. 2 a corresponding plant resulting from the revamping method of the invention. In FIG. 1 a conventional operation is shown, wherein a carbamate stream (c) from the recovery section (D) is recycled back to the synthesis section, viz. to the high pressure carbamate condenser (A). In comparison therewith, FIG. 2 shows the addition of a reactor (E) to which the carbamate recycle stream (c) is led, whereby the formed urea stream (h) is led to the high pressure carbamate condenser (A).

Figure 3:
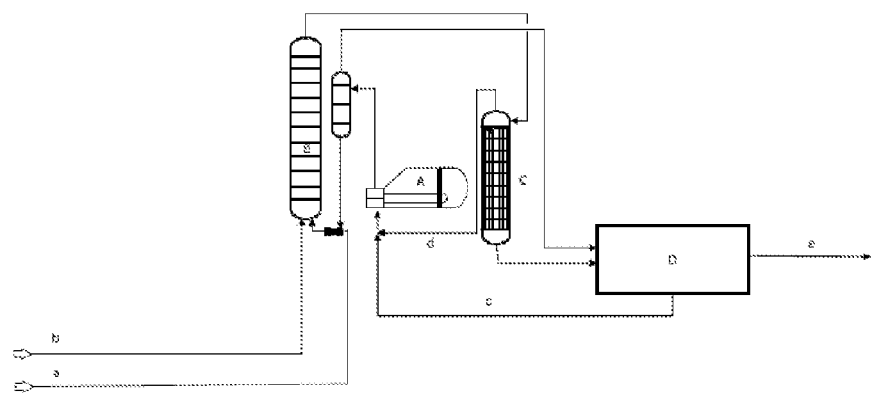
FIG. 3 and FIG. 4 are schematic drawings representing in FIG. 3 a conventional plant and in FIG. 4 a corresponding plant resulting from the revamping method of the invention.
Figure 4:
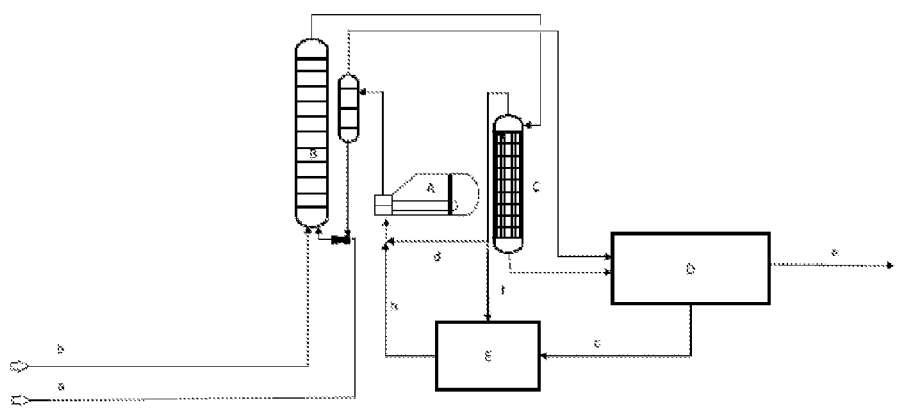

FIG. 3 is a schematic drawing of a conventional urea plant (similar to the configuration depicted in the block diagram of FIG. 1). Equally, FIG. 4 is a schematic drawing of a urea plant modified according to the invention (similar to the configuration depicted in the block diagram of FIG. 2).

Figure 5:
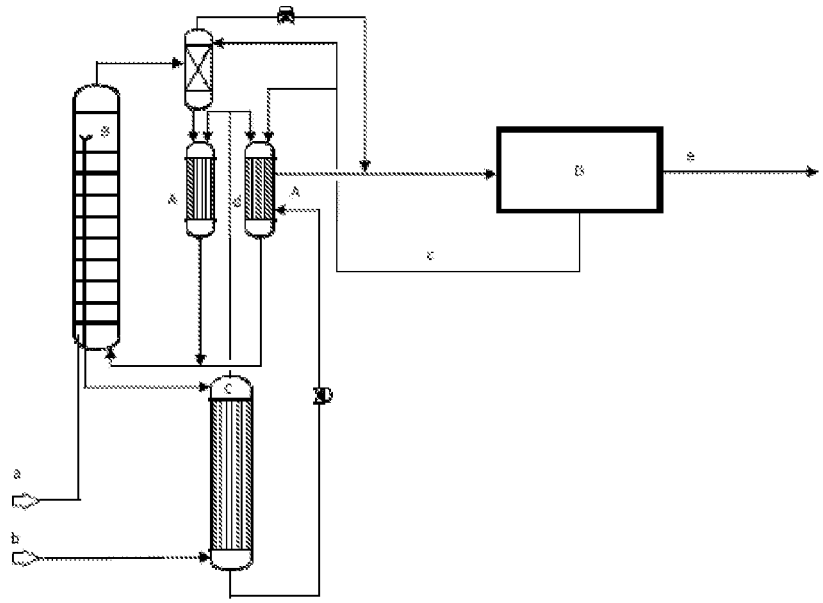
FIG. 5 and FIG. 6 are schematic drawings representing in FIG. 5 a conventional plant and in FIG. 6 a corresponding plant resulting from the revamping method of the invention.
Figure 6:
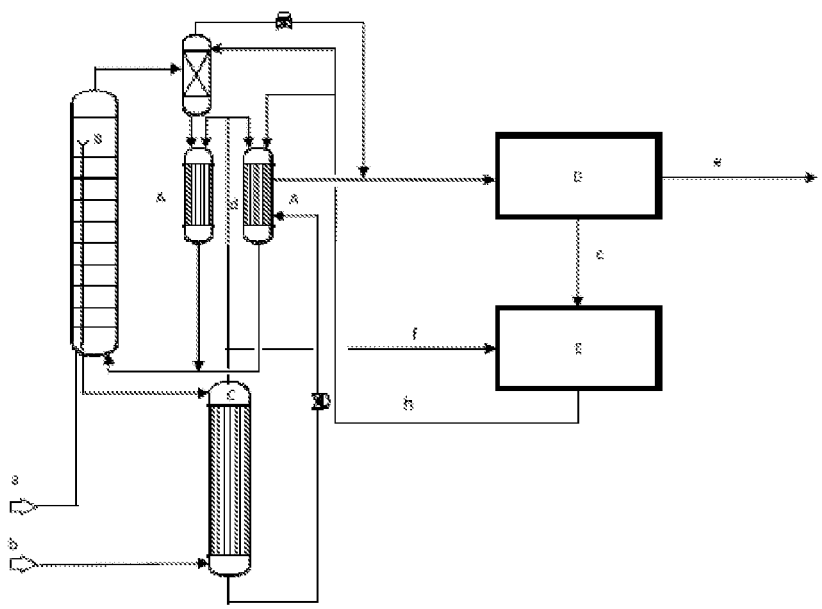

FIG. 5 is a schematic drawing of a conventional urea plant of the type having two high pressure carbamate condensers (A) in parallel. FIG. 6 is a schematic drawing showing the urea plant of FIG. 5 modified in accordance with the invention, viz. having an additional reactor (E) from which a stream of formed urea (h) is led to the condensers (A).

Figure 7:
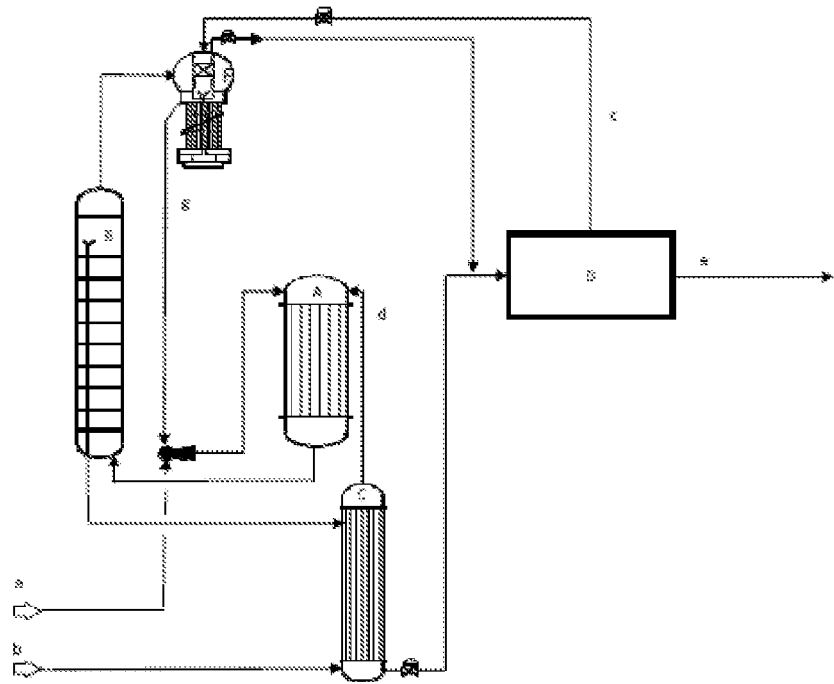
FIG. 7 and FIG. 8 are schematic drawings representing in FIG. 7 a conventional plant and in FIG. 8 a corresponding plant resulting from the revamping method of the invention.
Figure 8:
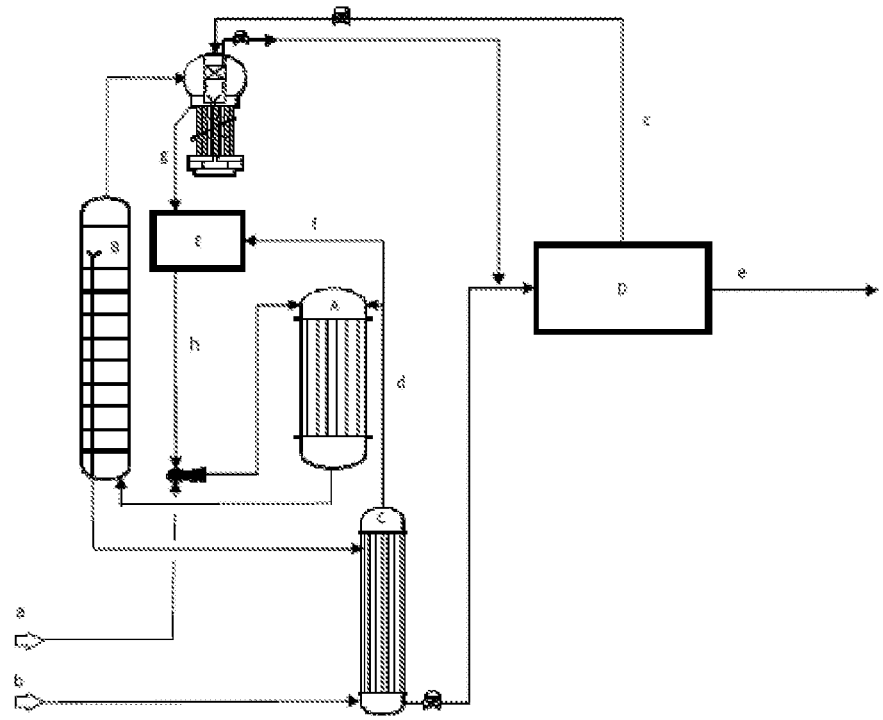

FIG. 7 is a schematic drawing of a conventional urea plant of the type having a high pressure scrubber (F) positioned downstream of the recovery section (D). FIG. 8 is a schematic drawing showing the urea plant of FIG. 7 modified in accordance with the invention, viz. having an additional reactor (E) positioned downstream of the scrubber (F). From the scrubber, a concentrated carbamate stream (g) is fed to the additional reactor (E).

The invention claimed is:

1. A method of increasing the production capacity of an existing urea plant, the existing plant comprising a high pressure carbamate condenser comprising a condensation chamber, a first reactor, a stripper, and a recovery section, wherein:
the condenser comprises a liquid outlet and a flow line to transfer liquid to a liquid inlet of the first reactor;
the first reactor comprises a liquid outlet and a flow line to transfer liquid to a liquid inlet of the stripper;
the stripper comprises a gas outlet and a flow line to transfer gas to a gas inlet of the condensation chamber of the condenser and a liquid outlet and a flow line to transfer liquid to the recovery section;
the recovery section comprises a liquid outlet and a flow line to transfer liquid to a liquid inlet of the condenser;
the method comprising installing a second reactor and flow lines, such that the second reactor has a liquid inlet for intake of liquid from a flow line from the liquid outlet of the recovery section, a liquid outlet and a liquid flow line to transfer urea-containing solution from said liquid outlet of the second reactor to a liquid inlet of said condensation chamber of the condenser.

2. A method according to claim 1, wherein a high pressure scrubber is positioned between the urea recovery section and the additional reactor, wherein said high pressure scrubber:
comprises an outlet and flow line to transfer carbamate solution to an inlet of the second reactor; and
has an inlet for recovering gas from a gas outlet of the first reactor.

3. A method according to claim 1, wherein the additional reactor comprises a vertical reactor.

4. A method according to claim 1, wherein an ejector is present between the additional reactor and the high pressure carbamate condenser.

5. A method according to claim 1, wherein the additional reactor is placed on ground level.

6. A method according to claim 1, wherein the additional reactor is designed for counter-current operation.

7. A method according to claim 1, wherein the second reactor comprises a gas inlet for intake of gas from the gas outlet of the stripper.

* * * * *